(12) United States Patent
Hera et al.

(10) Patent No.: US 10,849,639 B2
(45) Date of Patent: *Dec. 1, 2020

(54) RETRIEVAL DEVICES AND RELATED METHODS OF USE

(71) Applicant: Boston Scientific Scimed, Inc., Maple Grove, MN (US)

(72) Inventors: Mark Andrew Hera, Holden, MA (US); Kenneth M. Flynn, Woburn, MA (US); Manjunath L. Penagondla, Karnataka (IN); Prateet Verma, Irvine, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 142 days.

This patent is subject to a terminal disclaimer.

(21) Appl. No.: 16/116,756

(22) Filed: Aug. 29, 2018

(65) Prior Publication Data

US 2018/0368864 A1 Dec. 27, 2018

Related U.S. Application Data

(63) Continuation of application No. 14/964,002, filed on Dec. 9, 2015, now Pat. No. 10,111,677.

(60) Provisional application No. 62/090,493, filed on Dec. 11, 2014.

(51) Int. Cl.
*A61B 17/221* (2006.01)
*A61B 17/50* (2006.01)

(52) U.S. Cl.
CPC ............ *A61B 17/221* (2013.01); *A61B 17/50* (2013.01); *A61B 2017/2215* (2013.01)

(58) Field of Classification Search
CPC .................. A61B 17/50; A61B 17/221; A61B 2017/2212; A61B 2017/2215
See application file for complete search history.

(56) References Cited

U.S. PATENT DOCUMENTS

| | | | |
|---|---|---|---|
| 5,906,622 A | 5/1999 | Lippitt et al. | |
| 5,924,175 A | 7/1999 | Lippitt et al. | |
| 7,041,108 B2 | 5/2006 | Lippitt et al. | |
| 7,210,210 B2 | 5/2007 | Lippitt et al. | |
| 2015/0148814 A1* | 5/2015 | Chu ..................... | A61B 17/221 606/127 |
| 2019/0262026 A1* | 8/2019 | Uihlein ............ | A61B 17/32056 |

FOREIGN PATENT DOCUMENTS

WO WO 2013/050880 A2 4/2013

* cited by examiner

*Primary Examiner* — Ashley L Fishback
(74) *Attorney, Agent, or Firm* — Bookoff McAndrews, PLLC

(57) ABSTRACT

A retrieval device may have a contracted state and an expanded state and may include a sheath defining a longitudinal axis; a first arm, a second arm, and a third arm; a first member extending between a distal end of the first arm and a distal end of the third arm; and a second member extending between a distal end of the second arm and the distal end of the third arm. In the expanded state and from a distal-end view, the first and second members and the distal ends of the first arm, second arm, and third arm may form a V-shape with an open mouth.

16 Claims, 8 Drawing Sheets

RETRIEVAL DEVICES AND RELATED METHODS OF USE

CROSS-REFERENCE TO RELATED APPLICATIONS

This application is a continuation of U.S. application Ser. No. 14/964,002, filed Dec. 9, 2015, which claims the benefit of priority under 35 U.S.C. § 119 to U.S. Provisional Patent Application No. 62/090,493, filed Dec. 11, 2014, the entirety of which is each of which is incorporated herein by reference.

TECHNICAL FIELD

Various embodiments of the present disclosure relate generally to retrieval devices and related systems and methods. More specifically, the present disclosure relates to devices, systems, and methods for retrieving objects within a patient.

BACKGROUND

Retrieval devices are often used to remove organic material (e.g., blood clots, tissue, and biological concretions such as urinary, biliary, and pancreatic stones) and inorganic material (e.g., components of a medical device or other foreign matter), which may obstruct or otherwise be present within a patient's body cavities or passages. For example, concretions can develop in certain parts of the body, such as in the kidneys, pancreas, ureter, and gallbladder. Minimally invasive medical procedures are used to remove these concretions through natural orifices, or through an incision, such as during a percutaneous nephrolithotomy (PNCL) procedure. Further, lithotripsy and ureteroscopy, for example, are used to treat urinary calculi (e.g., kidney stones) in the ureter of a patient.

Retrieval devices may include end effectors for grasping and manipulating objects. An exemplary end effector may have a plurality of arms that expand and contract to grasp objects within a patient.

SUMMARY

Embodiments of the present disclosure relate to, among other things, retrieval devices and related systems and methods. Each of the embodiments disclosed herein may include one or more of the features described in connection with any of the other disclosed embodiments.

According to one example, a retrieval device may have a contracted state and an expanded state. The retrieval device may include a sheath defining a longitudinal axis; a first arm, a second arm, and a third arm; a first member extending between a distal end of the first arm and a distal end of the third arm; and a second member extending between a distal end of the second arm and the distal end of the third arm. In the expanded state, from a distal-end view, the first and second members and the distal ends of the first arm, second arm, and third arm may form a V-shape with an open mouth.

Additionally or alternatively, the retrieval device may include one or more of the following features: each of the first and second members may include a preformed bend; the first member may include at least two preformed bends, and in the expanded state, the portion of the first member between the at least two preformed bends may form a first leg of the V-shape; the second member may include at least two preformed bends, and in the expanded state, the portion of the second member between the at least two preformed bends may form a second leg of the V-shape; the third arm may be fixed parallel to the longitudinal axis; in the contracted state, each of the first, second, and third arms may be parallel to the longitudinal axis; the first member may extend from a distal end of the sheath, through the first arm, and into the distal end of the third arm; the second member may extend from the distal end of the sheath, through the second arm, and into the distal end of the third arm; and in an expanded state, a proximal end of the first arm and a proximal end of the second arm may be spaced apart from the sheath.

According to another example, a retrieval device may have a contracted state and an expanded state and may include a sheath defining a longitudinal axis and a first arm, a second arm, and a third arm. In the contracted state, each of the first, second, and third arms may be parallel to the longitudinal axis, and in the expanded state the third arm may parallel to the longitudinal axis and each of the first and second arms may form an angle with the longitudinal axis.

Additionally or alternatively, the retrieval device may include one or more of the following features: a first member may extend between a distal end of the first arm and a distal end of the third arm; a second member may extend between a distal end of the second arm and the distal end of the third arm; in the expanded state, from a distal-end view, the first and second members and the distal ends of the first arm, second arm, and third arm may form a V-shape with an open mouth; each of the first and second members may include a preformed bend; the first member may include at least two preformed bends, and in the expanded state, the portion of the first member between the at least two preformed bends may form a first leg of the V-shape; the second member may include at least two preformed bends, and in the expanded state, the portion of the second member between the at least two preformed bends may form a second leg of the V-shape; the first member may extend between the sheath and a proximal end of the first arm; the second member may extend between the sheath and a proximal end of the second arm; the first member may extend through the first arm and through the third arm; the second member may extend through the second arm and through the third arm; and the third arm may be a tubular member fixed relative to the sheath.

Another example of a retrieval device having a contracted state and an expanded state may include a sheath; a drive member within the sheath; a first arm, a second arm, and a third arm; and a positioner located, in the expanded state, within a space bounded by the first, second, and third arms.

Additionally or alternatively, the retrieval device may include one or more of the following features: the positioner may include a balloon; the positioner may include an expanding member having a preformed shape; the positioner may include at least one member extending between the sheath and an interior surface of at least one of the first, second, or third arms; and the retrieval device may further comprise at least one member extending between distal ends of at least two of the first, second, or third arms.

It may be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate exemplary embodiments of the present disclosure and together with the description serve to explain the principles of the disclosure.

DETAILED DESCRIPTION

Overview

The present disclosure is drawn to retrieval devices and related systems and methods. Reference will now be made in detail to embodiments of the present disclosure, examples of which are illustrated in the accompanying drawings. Wherever possible, the same reference numbers will be used throughout the drawings to refer to the same or like parts. The term "distal" refers to a portion farthest away from a user when introducing a device into a patient. By contrast, the term "proximal" refers to a portion closest to the user when placing the device into the patient.

EXEMPLARY EMBODIMENTS

First Exemplary Embodiment

General Overview

Figure 1:
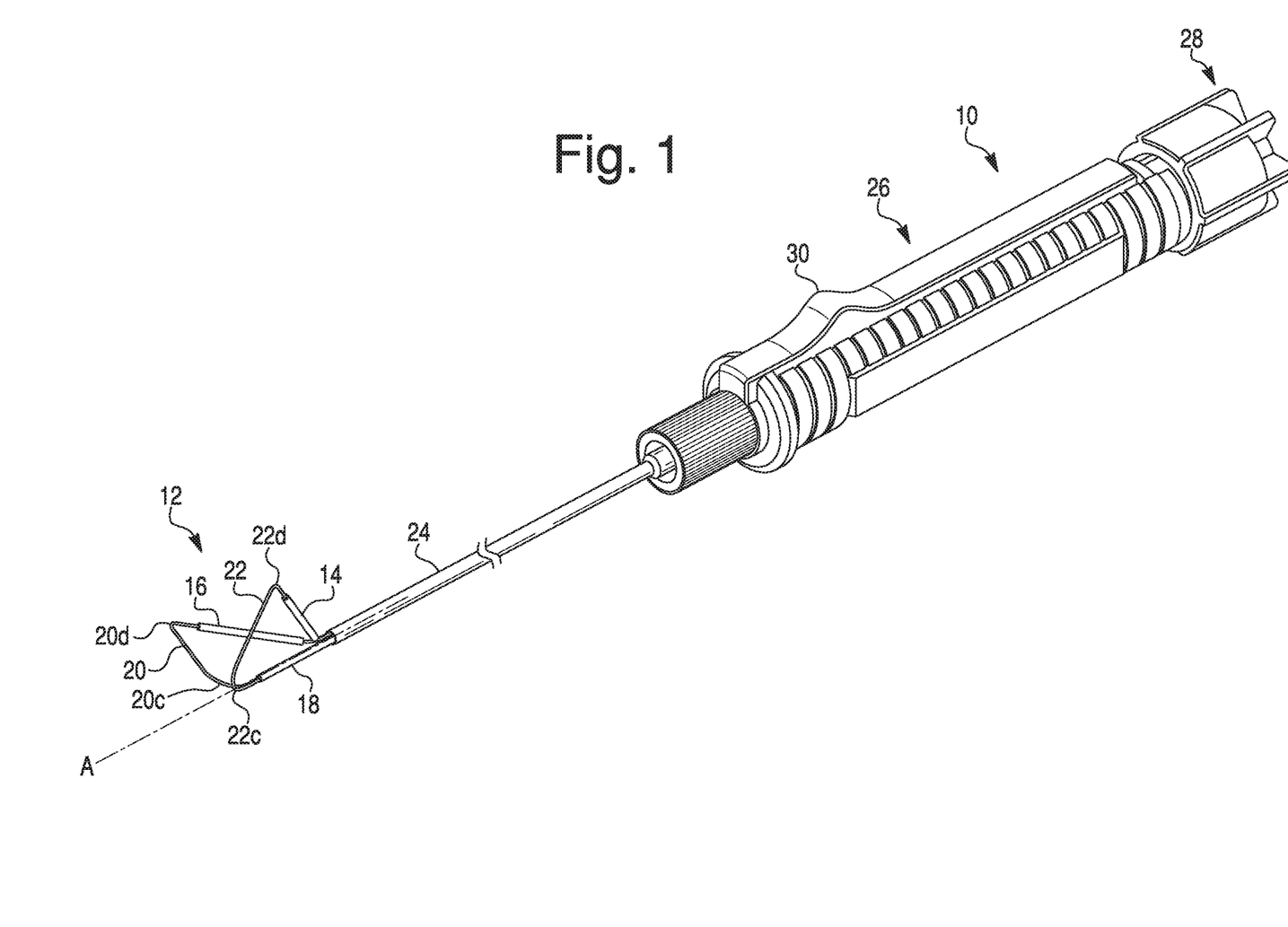
FIG. 1 is a retrieval device with an end effector in an expanded state, according to a first exemplary embodiment.
Figure 2:
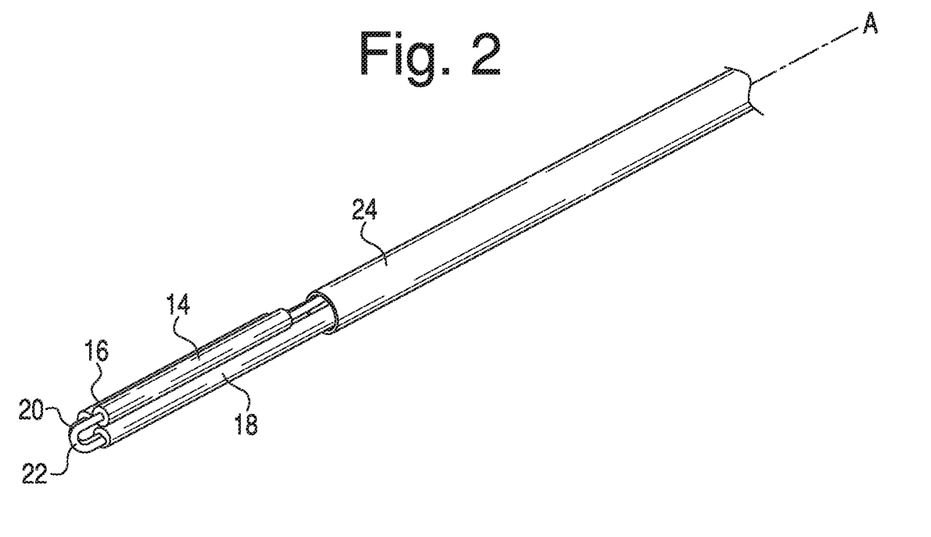
FIG. 2 is a partial view of the retrieval device of FIG. 1, shown with the end effector in a contracted state, according to an exemplary embodiment.

FIG. 1 shows a full view of a retrieval device 10 with an end effector 12 and handle assembly 26. In general, the end effector 12 may include a first arm 14, a second arm 16, and a third arm 18, generally referred to herein as arms 14, 16, 18. The end effector 12 may further include a first member 22 and a second member 20, generally referred to herein as members 22, 20. The arms 14, 16, 18 may be movable with respect to each other to grasp or reposition objects within a patient. The members 22, 20 may pass through the arms 14, 16, 18 and may be controlled by an actuator to transition the arms of the end effector 12 between an expanded state (FIG. 1) and a contracted state (FIG. 2). In various embodiments, the members 22, 20 may be movable relative to one or more of the arms 14, 16, 18.

The handle assembly 26 may be disposed at the proximal end 28 of the retrieval device 10. Handle assembly 26 may include an actuator 30 such as, for example, a sliding mechanism, rotating mechanism, pushing mechanism, scissor grip, or the like that may function to move the members 22, 20 to expand and contract the end effector 12. The actuator 30 may be coupled to a drive member 32 (FIG. 3), which may in turn be coupled to the members 22, 20. It is understood that the handle assembly may be formed in any conventional manner to control the movement of members 22, 20 relative to the sheath 24 or arms 14, 16, 18.

Figure 3:
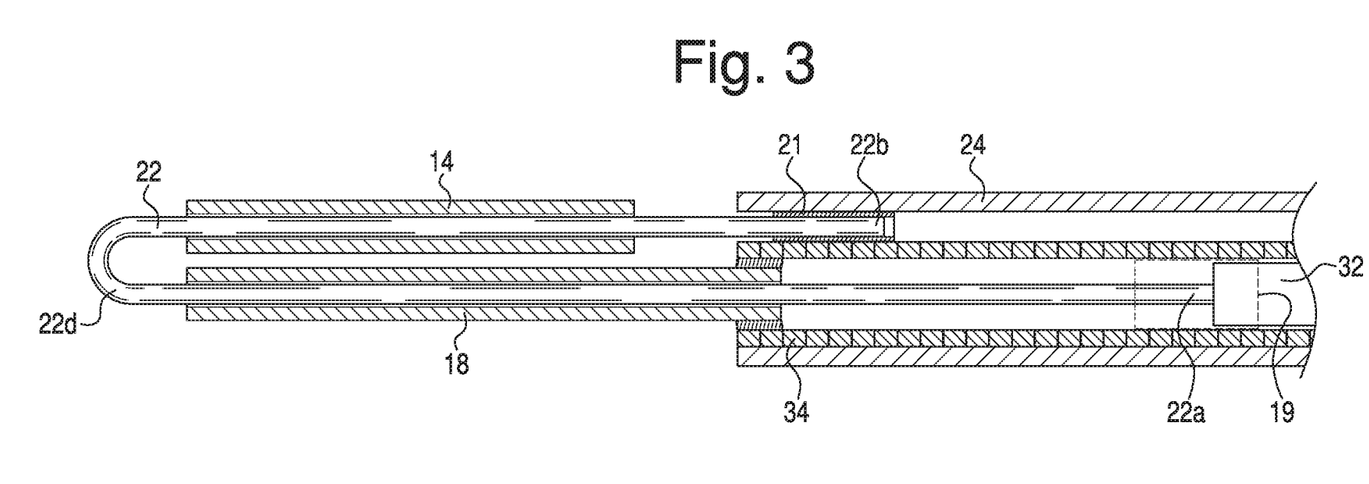
FIG. 3 is a cross-sectional view of the interior of the retrieval device of FIG. 1, according to an exemplary embodiment.

With reference to FIGS. 1-3, sheath 24 of the retrieval device may house the drive member 32, portions of members 22, 20, and in some embodiments, a proximal portion of third arm 18. The sheath 24 may include a lumen extending longitudinally therethrough and may define a longitudinal axis A. The sheath 24 may be, for example, a hollow tube of about 1.9 French, although the dimensions may differ based on the type of procedure being performed with the retrieval device 10. The sheath 24 may be made of a polymer material or combination of materials.

Retrieval Device Components

FIG. 1 illustrates the end effector 12 in an expanded state. In one embodiment of the expanded state, the third arm 18 may be parallel to the longitudinal axis A defined by the sheath 24, and the first arm 14 and the second arm 16 may form an angle with the longitudinal axis. A portion of first member 22 may extend between a distal end of sheath 24 and a proximal end of first arm 14, and a portion of second member 20 may extend between the distal end of sheath 24 and a proximal end of second arm 16. However, in other embodiments described below, the first and second members 22, 20 may extend between the exterior or other portions of sheath 24 and the proximal ends of arms 14, 15. FIG. 2 illustrates a contracted state of the end effector 12 shown in FIG. 1. In the contracted state, each of the first arm 14, second arm 16, and third arm 18 may be aligned parallel to the longitudinal axis A defined by the sheath 24.

In one embodiment, the end effector arms 14, 16, 18 may be tubular members defining lumens that receive one or both of members 22, 20. For example, arm 14 may receive member 22, arm 16 may receive member 20, and arm 18 may receive members 22 and 20. The first member 22 may extend through first arm 14 and into a distal end of the third arm 18, and the second member 20 may extend through second arm 16 and into a distal end of third arm 18. From the distal end of third arm 18, the first and second members 22, 20 may continue proximally through the lumen of third arm 18. In one embodiment, each arm 14, 16, 18 is movable with respect to the one or more members 20, 22 within its lumen. However, in other embodiments (e.g., with different internal mechanisms), one or more of arms 14, 16, or 18 may be fixed to the member 20 or 22 within its lumen.

The third arm 18 may be fixed relative to sheath 24, and arms 14, 16 may be movable relative to sheath 24 to enable opening and closing of the end effector 12. Arm 18 may be coupled to the distal end of sheath 24 by an adhesive or by any other suitable structure or material for joining the two components. Arms 14, 16 may be separated from or spaced apart from sheath 24 and in one embodiment may be connected to the sheath 24 only by members 22, 20, respectively. Thus, the arms 14, 16 may be indirectly connected to sheath 24. The indirect connection between arms 14, 16 and sheath 24 may allow the end effector 12 to extend to specific shapes and to possibly grasp objects that may not be obtainable if the arms 14, 16 were directly connected to sheath 24. In alternative embodiments, however, arm 18 may be movable relative to sheath 24, or one of arms 14 or 16 may be fixed relative to the sheath 24.

In one embodiment, the third arm 18 may be a tubular member coupled to a distal end of the sheath 24. The coupled third arm 18 may be fixed relative to the sheath 24 such that the arm 18 is parallel to the longitudinal axis A defined by the sheath 24. In an alternative embodiment, however, the third arm 18 may be a portion of sheath 24 that extends alongside the first and second arms 14, 16 when the retrieval device is in a contracted state. In other words, a distal portion of the sheath 24 may define the third arm 18 such that the third arm 18 and the sheath 24 are continuous and integral components. The first and second arms 14, 16 may contract against the distal portion of the sheath 24 when the end effector 12 is transitioning from an expanded to a contracted state. In this alternative embodiment, members 22, 20 may extend between the proximal ends of arms 14, 16 and attach to the exterior of sheath 24, instead of entering the lumen of sheath 24.

The arms 14, 16, 18 may be made of any suitable material or combination of materials, including a polymer such as polyimide or polyethylene terephthalate. In one embodiment, the arms 14, 16, 18 may be rigid such that in both the expanded and contracted state, the arms 14, 16, 18 may maintain a straight configuration. In other embodiments, the arms 14, 16 may be flexible and the arm 18 may maintain a straight configuration. In yet another embodiment, each of arms 14, 16, 18 may be flexible.

The arms 14, 16, and 18 may have a round or circular cross-sectional shape. In other embodiments, the arms 14, 16, and 18 may have an ellipsoid, square, rectangular, polygonal, or irregular cross-sectional shape. One or more of the arms 14, 16, 18 may include a portion flattened, machined, extruded, drawn, or etched into a different profile than a remaining portion to facilitate gripping of stones or other objects from within a patient. The exterior surfaces of one or more of the arms 14, 16, 18 may be roughened, notched, slotted, etched, sand-blasted, or otherwise modified to provide a better gripping surface.

One or more of the arms 14, 16, 18 may have an inner diameter of about 0.1143 millimeters, a wall thickness of about 0.0254 millimeters, and/or a length of about 19.5 millimeters, although other suitable dimensions may alternatively be utilized.

The members 20, 22 may be elongated wires and each may include at least one preformed bend. Referring to FIGS. 1 and 3, the wires may include preformed bends 20c, 20d, 22c, and 22d. Each member 20, 22 may further include an unlabeled bend near the proximal ends of arms 16, 14, respectively, in the expanded state shown in FIG. 1. Each preformed bend may be biased in the bent position to facilitate expansion of the end effector 12.

According to examples of the present disclosure, the members 20, 22 can be made at least partially of a shape-memory material. Shape-memory material is a material that can be formed into a particular shape, retain that shape during resting conditions (e.g., when the shaped material is not subject to external forces or when external forces applied to the shaped material are insufficient to substantially deform the shape), be deformed into a second shape when subjected to a sufficiently strong external force, and revert substantially back to the initial shape when external forces are no longer applied. Examples of shape memory materials include synthetic plastics, stainless steel, and superelastic metallic alloys of nickel/titanium (e.g., Nitinol), copper, cobalt, vanadium, chromium, iron, or the like.

In one embodiment, the preformed bends of each member 20, 22 are configured such that the end effector 12 in an expanded state assumes a "butterfly" configuration. In other words, the expanded end effector 12 may generally form two similar three-sided shapes with complete outer boundaries. One of the boundaries may be shared by the two three-sided shapes. The first shape of the "butterfly" may be formed by third arm 18, first arm 14, and an exposed portion of first member 22. First member 22 may extend between a distal end of first arm 14 and a distal end of third arm 18. The exposed portion of first member 22 may be generally straight or may have a curved or bowed configuration. The second triangle of the butterfly may be formed by third arm 18, second arm 16, and an exposed portion of second member 20. Second member 20 may extend between a distal end of second arm 16 and the distal end of third arm 18. The exposed portion of second member 20 may be generally straight or may have a curved or bowed configuration.

From a distal-end view of the retrieval device 10 (e.g., looking from the distal end to the proximal end along axis A), the end effector 12 may form a V-shape with an open mouth. The exposed portions of first member 22 and second member 20 may each form a "leg" of the V-shape. In one embodiment, the portion of first member 22 between preformed bends 22c and 22d may form a first leg of the V-shape, and the portion of second member 20 between preformed bends 20c and 20d may form a second leg of the V-shape. The distal end of the third arm 18 may form the point of the V-shape, and the distal ends of each of the first arm 14 and the second arm 16 may form the "ends" of the V-shape (i.e., the distal end of arm 14 may correspond to the free end of one leg of the V-shape, and the distal end of arm 16 may correspond to the free end of the other leg of the V-shape). The open "mouth" of the V-shape may be the opening between the distal end of arm 14 and the distal end of arm 16 when viewing the retrieval device 10 from a distal-end perspective.

The open mouth of the V-shape may be formed because there is no member directly connecting the distal ends of first arm 14 and second arm 16. In contrast, member 22 may directly connect the distal end of first arm 14 to the distal end of third arm 18, and member 20 may directly connect the distal end of second arm 16 to the distal end of third arm 18. In some embodiments, however, one of the first or second members 20, 22 or a separate third member may directly connect the proximal ends of first arm 14 and second arm 16, or may connect arms 14, 16 at an intermediate location between the proximal and distal ends of the arms. For example, a member may connect arms 14, 16 about halfway between the proximal and distal ends of the arms.

The open mouth portion of the expanded end effector 12, between the distal ends of arms 14 and 16, may facilitate grasping of objects and may allow for stones (or other objects) to be easily dropped or repositioned. These features may be useful during lithotripsy procedures. The open V-shape may further prevent large objects from getting lodged in the end effector 12. When objects become lodged in an end effector, removal of the device may be difficult, potentially causing danger to the patient. Another feature of the butterfly configuration is that in some embodiments the end effector 12 may open and close without the end effector 12 portion moving in and out of the sheath 24 or along longitudinal axis A. Some existing basket devices open and close by moving longitudinally. The longitudinal movement could, in some cases, cause difficulty capturing objects. However, the arms of the end effector 12, in some embodiments, can be placed around an object and closed without moving longitudinally within the body lumen. Finally, the butterfly configuration may allow for capture of objects located near the distal end of the end effector 12 or objects located towards a side of the end effector 12. In contrast, some existing basket devices require objects to be captured only from the side of the basket.

The preformed bends of the members 22, 20 may facilitate the V-shape of the expanded end effector 12. The angles of each bend may be configured to cause arms 14, 16, 18 to assume the V-shape when one or more preformed bends of members 22, 20 become free from the confines of sheath 24 or arms 14, 16, 18 during transition of the end effector 12 from the contracted to the expanded state. The preformed bends of members 22, 20 may further be configured to cause the members 22, 20 to turn along an axis, which may cause arms 14, 16 to expand away from each other when transitioning from the contracted state to the expanded state.

FIG. 3 illustrates a cross-sectional view of the retrieval device 12 shown in FIGS. 1 and 2. For simplicity, a few internal features of the end effector 12 (e.g., cable 34) visible in FIG. 3 are not shown in FIG. 2. Referring to FIG. 3, although member 20 is hidden behind member 22, each member 20, 22 may have a first end 20a, 22a, respectively, and a second end, 20b, 22b, respectively. In one embodiment, first ends 20a and 22a of members 20, 22 may be coupled to the drive wire 32 within sheath 24. The attachment may be provided by one or more of a splice joint, adhesives, melting, welding, crimping, and/or any other suitable attachment mechanism. A sleeve 19 may be placed over the first ends 20a, 22a and the distal portion of the drive member 32 to secure the elements together. The sleeve 19 may be made of a polytetrafluoroethylene like TEFLON. The sleeve 19 may be heat shrinkable onto the first ends 20a, 22a and the drive member 32.

The second ends 20b, 22b of members 20, 22 may terminate near a distal end of sheath 24 and may be fixed to sheath 24 and cable 34. The attachment may be provided by one or more of a splice joint, adhesives, melting, welding, crimping, and/or any other suitable attachment mechanism. In one embodiment, a sleeve 21, similar to sleeve 19, may be placed over the second ends 20b, 22b and attached to the sheath 24 via the above-listed attachment mechanisms. If the third arm 18 is a separate tubular member fixed to the sheath 24, the second ends 20b, 22b may be fixed to the interior of sheath 24 and exterior of cable 34, as shown in FIG. 3. If the third arm 18 is a distal portion of sheath 24, however, the second ends 20b, 22b may be fixed to the exterior of sheath 24.

As noted above, the retrieval device 10 may further include a cable 34. In one embodiment, the cable 34 is a Bowden cable. The arm 18 may be fixed relative to the cable 34, and the ends 20b, 22b may be sandwiched between sheath 24 and cable 34. In an alternative embodiment, the retrieval device may not include cable 34, and the arm 18 may be coupled directly to the sheath 24.

In an alternative embodiment, the two first ends 20a, 22a may fixed to the interior of the sheath 24, and the two second ends 20b, 22b may fixed to the drive member 32. Thus, when the drive member 32 is pushed in a distal direction, the two second ends 20b, 22b are pushed in a distal direction, with the members 20, 22 moving through the arms 16, 14 to expand arms 16, 14 and the end effector 12. In this embodiment, the arm 18 may be fixed or movable relative to the members 20, 22.

In yet another alternative embodiment, as described above, the members 20, 22 may be configured to expand the end effector 12 when a distal portion of the sheath 24 forms the third arm 18. In this embodiment, the two first ends 20a, 22a may be fixed to the drive member 32, but the two second ends 20b, 22b may be fixed to the exterior of sheath 24. When the drive member 32 is pushed distally, the two first ends 20a, 22a are pushed in a distal direction, with the first and second members 22, 20 moving through the arm 18 to expand arms 14, 16 and the end effector 12. The first member 22 and the second member 20 may therefore be movable relative to the third arm 18. The arms 14, 16 may be fixed or movable relative to members 22, 20.

In a still further alternative embodiment of the retrieval device 10, second ends 20b, 22b of members 20, 22 may not be fixed to sheath 24. For example, second ends 20b, 22b may slide on a track or other mechanism that allows for proximal and distal movement. A stopper may be provided at a distal location on the track or on the interior of sheath 24 to prevent the ends 20b, 22b from exiting the sheath 24. In operation, pushing drive member 32 distally may push ends 20b, 22b distally along the track until the ends 20b, 22b reach the stopper. Once reaching the stopper, ends 20b, 22b would be prevented from further distal movement. As the user continued pushing drive member 32 and first ends 20a, 22a distally, members 20, 22 would begin expanding the arms 16, 14. In an alternative embodiment, ends 20b, 22b may be connected to form a U-shaped bend, and the stopper may stop the U-shaped bend from further distal movement. In yet another alternative embodiment, members 20 and 22 may be a continuous wire that forms a U-shaped bend in the vicinity of second sends 20b, 22b in FIG. 3. The U-shaped bend may be movable along a track and may contact a stopper or pin to maintain a coupling between the bend and the sheath 24.

During use, the end effector 12 may be inserted into a patient to retrieve material. The end effector 12 may be inserted in a contracted position, as shown in FIG. 2, through the lumen of a cystoscope, ureteroscope, or any other device used to gain access to the interior of the patient. In other embodiments, the end effector 12 may be inserted into the patient through an access sheath, without the use of another device. In yet other methods, the end effector 12 may inserted directly into a natural body lumen or incision.

Once inserted and positioned, the end effector 12 may be expanded. In one embodiment, the actuator 30 (FIG. 1) may be a sliding mechanism that a user may slide distally to expand the end effector 12. Referring to FIG. 3, sliding the actuator 30 distally may move the drive member 32 distally, which in turn pushes first ends 20a, 22a distally. The preformed bends on members 20, 22 may cause arms 16, 14, respectively, to flare away from the longitudinal axis A until reaching the expanded position shown in FIG. 1. During expansion, preformed bends 20c, 22c may exit the third arm 18, causing those portions of members 20, 22 to transition from a straight configuration to a bent configuration. Preformed bends near proximal ends of arms 16, 14 may also facilitate the V-shape configuration by directing arms 16, 14 radially outward from axis A. Once expanded, the end effector 12 may be further positioned such that material can be grasped by the arms 14, 16, 18.

To return the end effector 12 to a contracted state, the user may slide the actuator 30 proximally, causing the drive member 32 and first ends 20a, 22a to slide proximally. Members 20, 22 may be pulled proximally back through the arm 18. As members 20, 22 and their preformed bends 20c, 22c are pulled back into arm 18, arms 16, 14 may contract back towards axis A towards the contracted configuration shown in FIG. 2.

In alternative configurations of members 20, 22 described above, movement of the actuator 30 may similarly cause expansion and contraction of the end effector 12. For example, if first ends 20a, 22a are fixed to the interior of sheath 24 instead of to drive member 32, sliding or otherwise actuating the actuator 30 to expand the end effector 12 may include moving second ends 20b, 22b distally. Members 20, 22 may then move through arms 16, 14, with previously-confined preformed bends (e.g., 20d, 22d) causing the arms 16, 14 to expand. In this embodiment, the arm 18 may be fixed or movable relative to the members 20, 22. If the distal portion of sheath 24 forms third arm 18, movement of actuator 30 may cause movement of the first ends 20a, 22a and movement of members 20, 22 through third arm 18, while the second ends 20b, 22b of members 20, 22 remain fixed relative to sheath 24. If second ends 20b, 22b are slidable along a track or other mechanism, movement of actuator 30 may cause both first and second ends of members 20, 22 to move distally by a preset distance prior to expansion of the end effector 12.

Second Exemplary Embodiment

Figure 4:
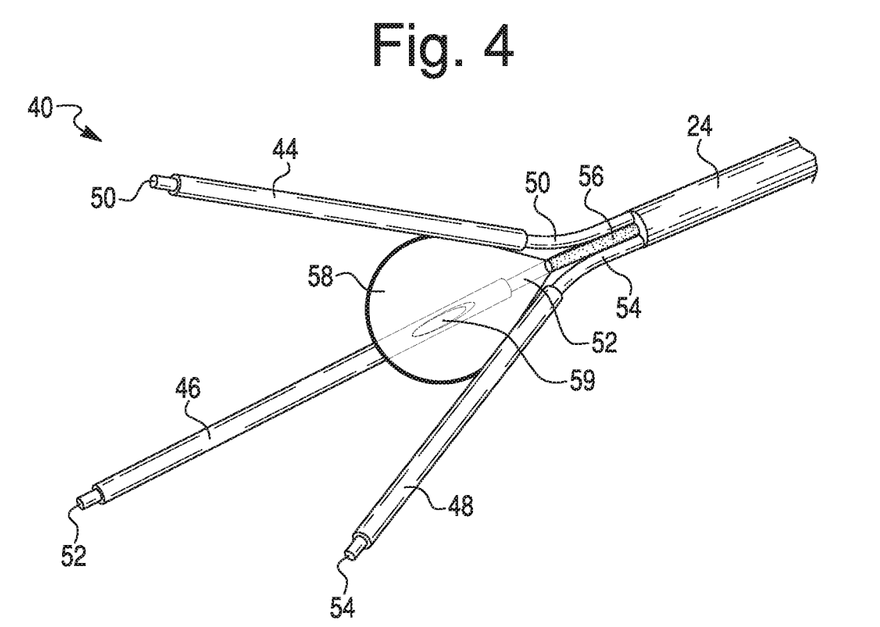
FIG. 4 illustrates an end effector of a retrieval device according to a second exemplary embodiment, shown in an expanded state.
Figure 5:
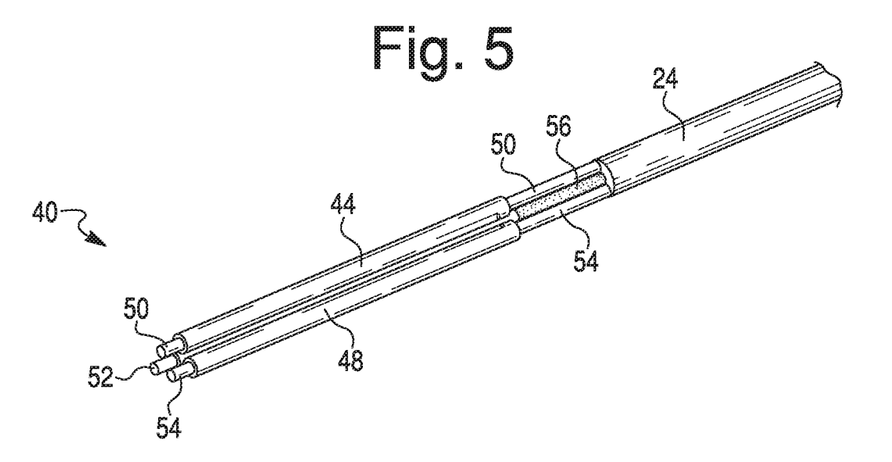
FIG. 5 illustrates the end effector of FIG. 4 in a contracted state, according to an exemplary embodiment.

FIGS. 4 and 5 illustrate a second embodiment of a retrieval device in expanded and contracted configurations, respectively. In this embodiment, an end effector 40 may extend from a sheath 24. The end effector 40 may include arms 44, 46, 48, which may share many characteristics with the arms 14, 16, 18 of FIG. 1. The end effector may further include members 50, 52, 54, which may share many characteristics with members 20, 22 of FIG. 1. The members 50, 52, 54 may extend through arms 44, 46, 48, respectively, and may protrude from the distal ends of their respective arms. In one embodiment, the members 50, 52, 54 are fixed relative to arms 44, 46, 48.

In the embodiment of FIG. 4, the end effector 40 may further include a positioner to aid in transitioning the end effector 40 between contracted and expanded states. The positioner may be located within a space bounded by arms 44, 46, 48. In one embodiment, the positioner may include a sheath 56 and a balloon 58. The sheath 56 may be coupled to a source of fluid, such as air or saline solution, to inflate the balloon 58 and may additionally or alternatively be coupled to a suction force to deflate the balloon 58. The balloon 58 may be coupled to the sheath 56 via a seal to allow fluid to flow between the sheath 56 and the balloon 58. The balloon 58 may further be coupled to one or more attachment points 59 on the interior of arms 44, 46, and 48. The attachment points 59 may be formed with glue, a thermal bond, or by any other suitable attachment structure or method. In an alternative embodiment, end effector 40 does not include a sheath 56 and the balloon may be coupled instead to a lumen within the sheath 24. Fluid may travel through the lumen during inflation and deflation of the balloon 58.

The end effector 40 may be used similarly to the embodiment of FIG. 1. The end effector 40 may be inserted into a patient in a contracted state, as shown in FIG. 5. Once inserted, a fluid source may be used to send fluid through sheath 56 (or a lumen within sheath 24) and into balloon 58, causing the balloon 58 to inflate and the end effector 40 to expand as shown in FIG. 4. The end effector 40 may then be positioned to grasp material.

The end effector 40 may be contracted by applying a source of suction to sheath 56 to remove fluid from balloon 58 and cause the arms 44, 46, 48 to return to the contracted position shown in FIG. 5. Additionally or alternatively, the members 50, 52, 54 may be biased in the straight position shown in FIG. 5. When biased in the straight position, the members 50, 52, 54 may cause arms 44, 46, 48 to return to the position shown in FIG. 5 when fluid pressure is removed from the balloon 58 of the expanded end effector 40. Additionally or alternatively, the balloon 58 may be preformed into a collapsed configuration. Thus, if fluid pressure is removed from an expanded balloon 58, the balloon 58 may return to a collapsed position and transition the arms 44, 46, 48 to the position shown in FIG. 5.

Third Exemplary Embodiment

Figure 6:
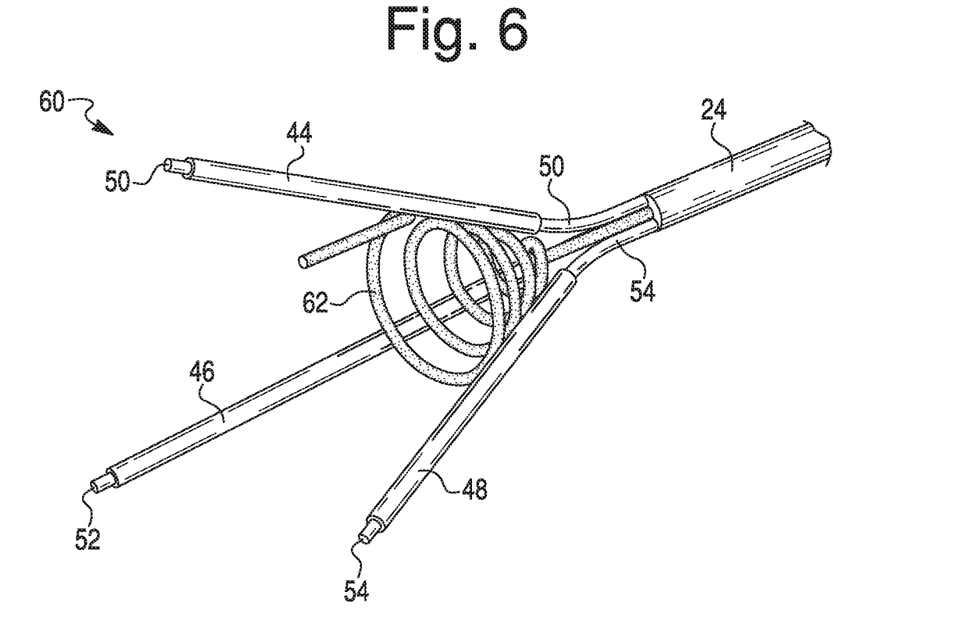
FIG. 6 illustrates an end effector of a retrieval device according to a third exemplary embodiment, shown in an expanded state.
Figure 7:
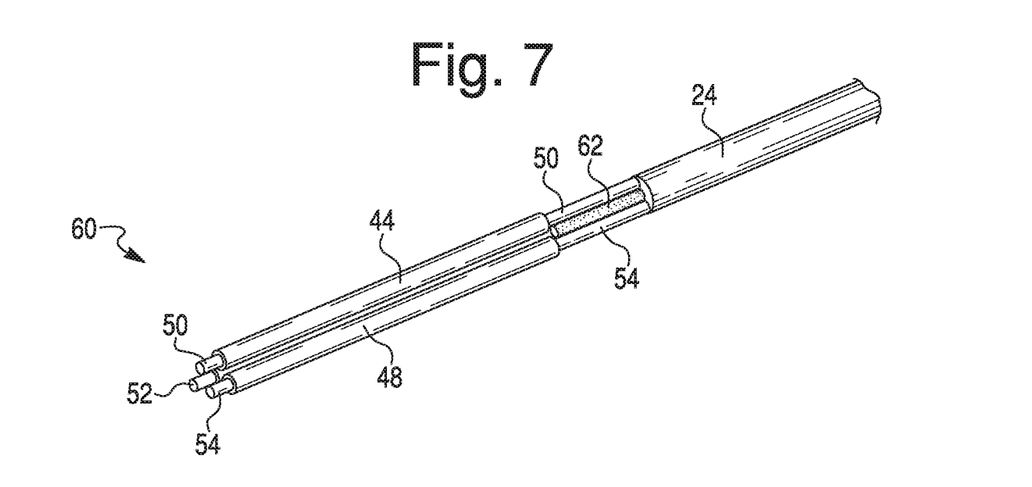
FIG. 7 illustrates the end effector of FIG. 6 in a contracted state, according to an exemplary embodiment.

FIGS. 6 and 7 illustrate a third embodiment of a retrieval device in expanded and contracted configurations, respectively. The end effector 60 may be similar to end effector 40 of FIGS. 4 and 5 in that it may include a sheath 24, arms 44, 46, 48, and members 50, 52, 54. End effector 60 may also include a positioner located within a space bounded by the arms 44, 46, 48. However, the positioner of end effector 60 may include a preformed expanding member 62, instead of a balloon 58, to transition the end effector 60 between expanded and contracted positions. A proximal end of the expanding member 62 may be coupled via a drive member to an actuator, such as actuator 30 shown in FIG. 1, that may be used to retract and extend expanding member 62 into and out of the sheath 24. In addition to the expanding member 62, the end effector 60 may include any other features described herein, such as biased members 50, 52, 52, to aid in expanding or contracting the end effector 60.

The expanding member 62 may be a wire made of any shape-memory material, such as Nitinol. In one embodiment, expanding member 62 is preformed into a spiral shape. The expanding member 62 alternatively may be preformed into any other shape that would expand to open arms 44, 46, 48 and would assume a generally straight configuration when retracted into sheath 24.

The end effector 60 may be used in a similar manner as other end effector embodiments described herein. To transition the end effector 60 from the expanded position shown in FIG. 6 to the contracted position shown in FIG. 7, an actuator may be used to retract expanding member 62 into a lumen of sheath 24. As the expanding member 62 is retracted into the sheath 24, it may assume a straightened configuration. The arms 50, 52, 54 may be inwardly biased such that they transition to the contracted configuration shown in FIG. 7 as the expanding member 62 is pulled into the sheath 24. The actuator may also be used to extend the expanding member 62 out of the lumen of the sheath 24. As the expanding member exits the sheath, it may assume its preformed spiral configuration, exerting pressure on arms 44, 46, 48 and causing them to transition to the expanded configuration shown in FIG. 6.

Fourth Exemplary Embodiment

Figure 8:
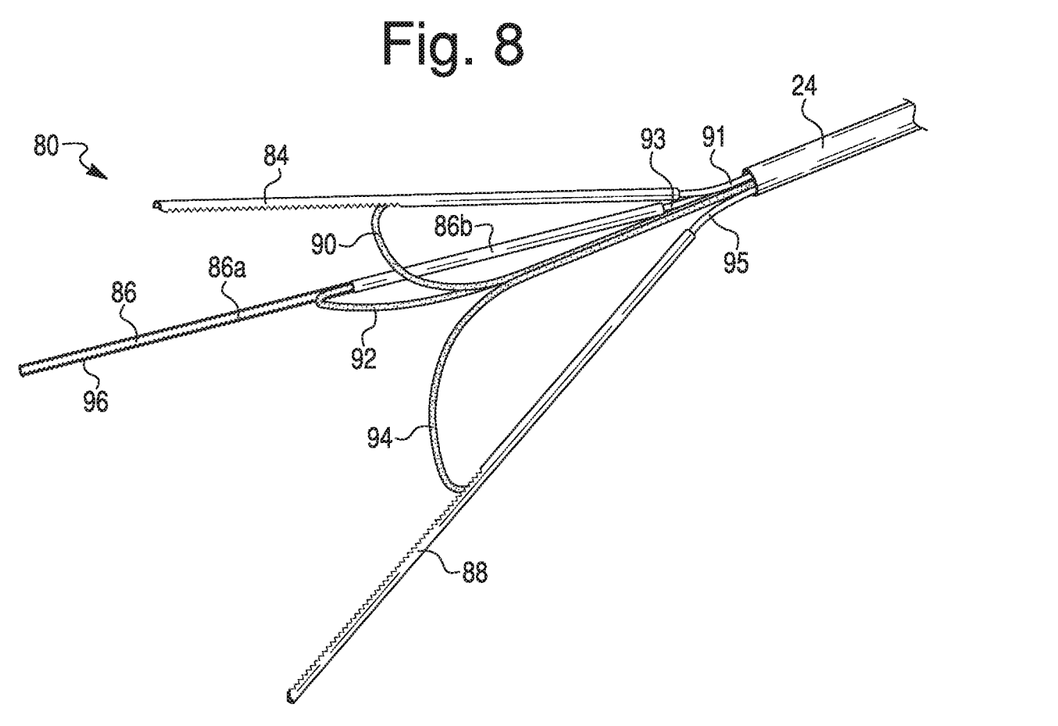
FIG. 8 illustrates an end effector of a retrieval device according to a fourth exemplary embodiment, shown in an expanded state.

FIG. 8 illustrates a fourth embodiment of a retrieval device in an expanded configuration. The end effector 80 of FIG. 8 extends from a sheath 24, similar to previous embodiments. The end effector 80 may include arms 84, 86, 88, which may be made of a polymer such as polyimide or polyethylene terephthalate. Each arm 84, 86, 88 may have an open distal portion, such as distal portion 86a of arm 86. The distal portions may have serrated edges, such as serrated edge 96 of arm 86. The serrated edge feature may be included in any of the embodiments disclosed herein. Each arm 84, 86, 88 may further have a proximal tubular portion, such as proximal portion 86b of arm 86.

End effector 80 may also have a positioner located in the space bounded by arms 84, 86, 88. The positioner may include at least one member 90, 92, or 94 extending between the sheath 24 and an interior surface of at least one of arms 84, 86, 88. In one embodiment, the positioner may include three members 90, 92, 94. The members 90, 92, 94 each may be fixed to their corresponding arms 84, 86, 88 near the transition point between the proximal and distal portions of the arms. Additionally or alternatively, members 90, 92, 94 may be fixed to the inward-facing surface or to the interior of their respective arms 84, 86, 88, and separate connecting wires 91, 93, 95 may extend between the proximal ends of arms 84, 86, 88 and the distal end of sheath 24. In an additional or alternative embodiment, the members 90, 92, 94 continue proximally through the proximal portions of the arms 84, 86, 88 and into the sheath 24, where they may be fixed. For example, member 92 may travel proximally through proximal portion 86b of arm 86, exit the proximal end of arm 86, and enter the sheath 24. Thus, members 91, 93, 95 may be continuous and integral with members 90, 92, 94, respectively.

Members 90, 92, 94 may extend inward from their respective arms toward a longitudinal axis A defined by sheath 24 (see FIG. 1). The separate members 90, 92, 94 may then travel proximally into sheath 24, where they may be connected to a drive member 32 (see FIG. 3). In an alternative embodiment, the separate members 90, 92, 95 may converge into a single wire or member before connecting to the drive member 32.

The end effector 80 may be generally used in a similar manner as other end effector embodiments described herein. An actuator, such as actuator 30, may be used to move drive member 32 to expand and contract the end effector 80. For example, if the drive member 32 is moved distally, members 90, 92, 94 may be pushed distally. The members 90, 92, 94 may be made of a shape-memory material, as described above, and may have a preformed curved shape that may cause the arms 84, 86, 88 to expand radially outward as shown in FIG. 8. When the drive member 32 is moved proximally, the members 90, 92, 94 may be pulled proximally, straightening the members 90, 92, 94 and causing the arms 84, 86, 88 to contract radially inward.

Fifth Exemplary Embodiment

Figure 9:
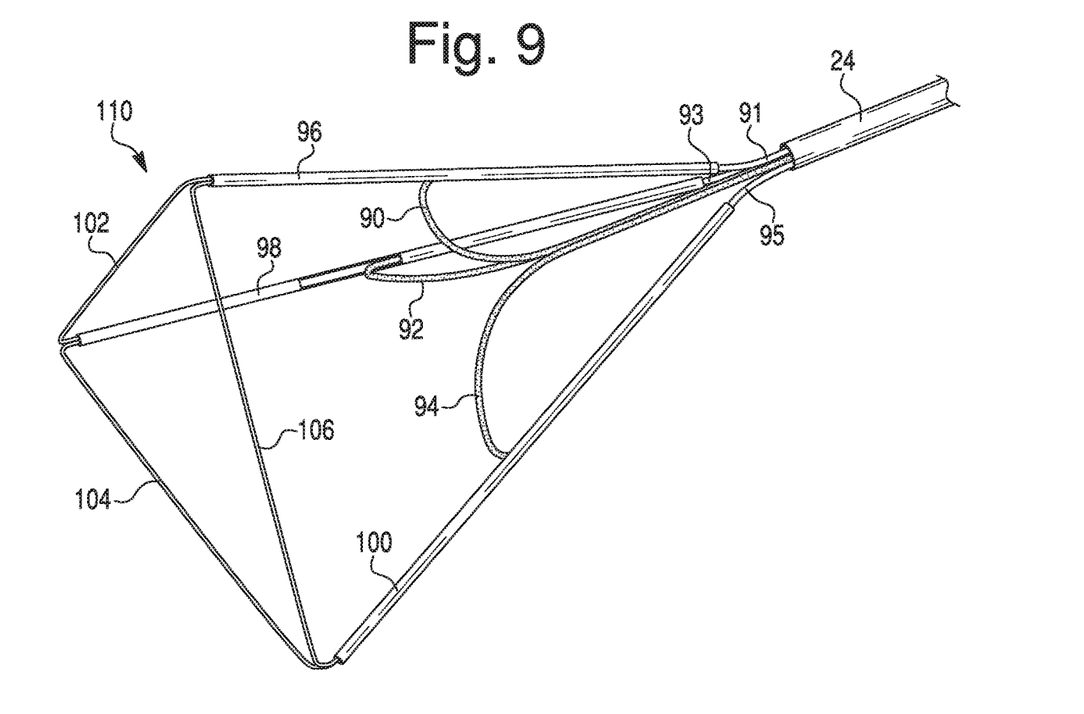
FIGS. 9-11 illustrate an end effector of a retrieval device according to a fifth exemplary embodiment, shown progressing from an expanded state to a contracted state.
Figure 10:
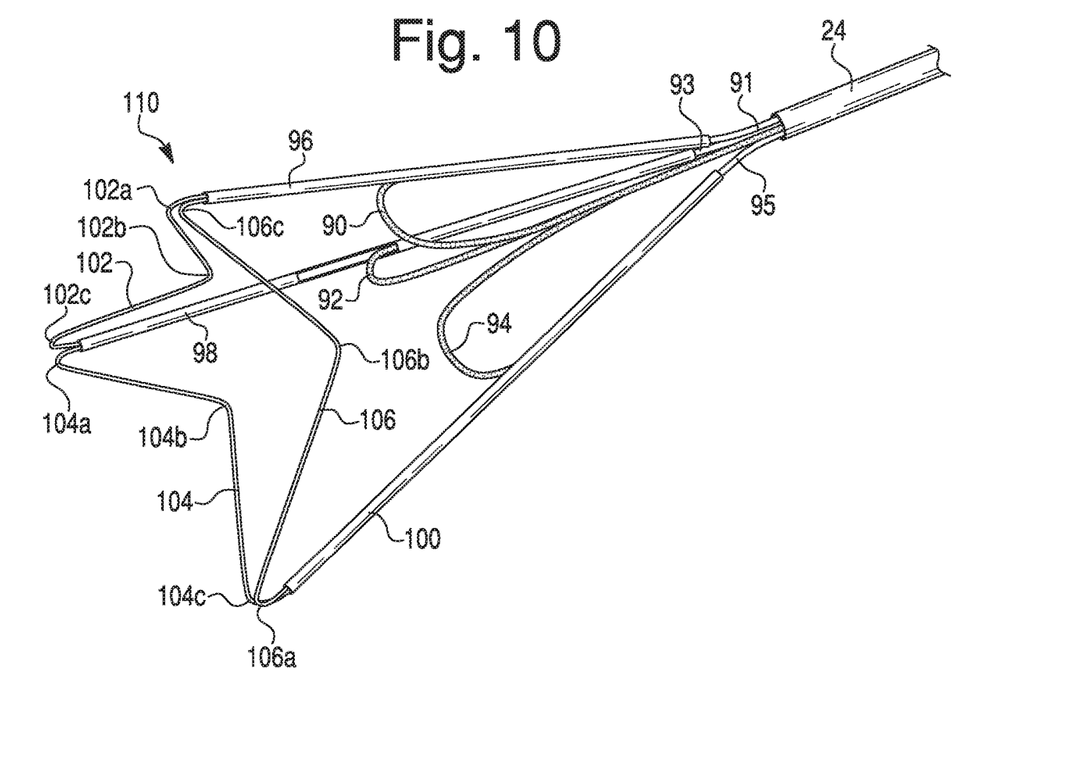
Figure 11:
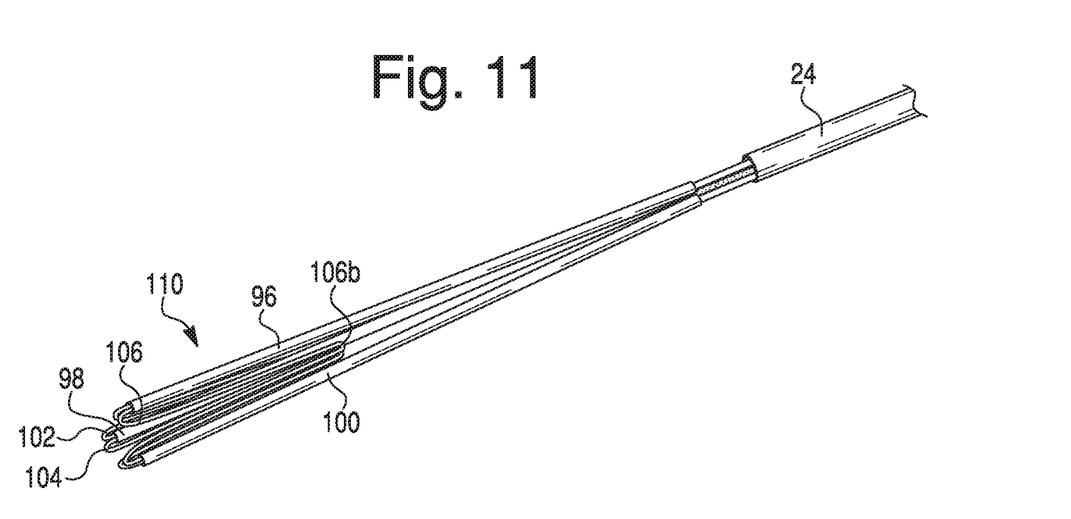

FIGS. 9, 10, and 11 illustrate a retrieval device of a fifth embodiment having an end effector 110. FIG. 9 shows the end effector 110 in a fully expanded state, FIG. 10 shows the end effector 110 in a partially contracted state, and FIG. 11 shows the end effector in a contracted state. End effector 110 is similar to effector 80 of FIG. 8 in that end effector 110 extends from a sheath 24 and includes three members 90, 92, 94. The members 90, 92, 94 may be coupled to the arms 96, 98, 100 of end effector 110 in a similar way as described in connection with end effector 80. The arms 96, 98, 100 are also similar to the arms 84, 86, 88 of end effector 80, except the arms 96, 98, 100 of FIG. 9 are shown with closed proximal and distal portions and without serrated edges. However, as noted above, the end effector embodiments described herein may each include any features described in connection with other end effector embodiments.

The embodiment of FIG. 9 differs from the embodiment of FIG. 8 in that the positioner of end effector 110 may include end members 102, 104, 106 connecting the distal ends of arms 96, 98, 100. For example, end member 102 may connect the distal ends of arms 96 and 98, end member 104 may connect the distal ends of arms 98 and 100, and end member 106 may connect the distal ends of arms 100 and 96. The end members 102, 104, 106 may be made of any shape-memory material, such as Nitinol. Each end member 102, 104, 106 may be fixed to the interiors of the arms that it connects.

Each end member 102, 104, 106 may be preformed to have three bends—one near the distal end of a first arm, one near the distal end of a second arm, and one about halfway between the two distal ends in an expanded state. For example, referring to FIG. 10, end member 102 may be preformed to have bend 102a near the distal end of arm 96, bend 102b about halfway between the distal ends of arms 96 and 98 when those arms are expanded, and bend 102c near the distal end of arm 98. The preformed bends may be biased in a bent position to facilitate contraction of end effector 110.

End effector 110 may be used in a similar manner to end effector 80. However, during contraction, the members 102, 104, 106 may bend as shown in FIGS. 10 and 11. As the end effector 110 contracts and members 90, 92, 94 are pulled into sheath 24, preformed bends 102b, 104b, 106b extend proximally. The members 102, 104, 106 may help retain material, such as stones, within the interior portion of end effector 110.

The disclosed retrieval devices may be utilized in any suitable application requiring the capture and removal of materials from the body. Any aspect set forth in any embodiment may be used with any other embodiment set forth herein. The devices may be used in any suitable medical procedure, may be advanced through any suitable body lumen and body cavity, and may be used to remove material from any suitable body portion. For example, the devices described herein may be used through any natural body lumen or tract, including those accessed orally, vaginally, rectally, nasally, urethrally, or through incisions in any suitable tissue.

It will be apparent to those skilled in the art that various modifications and variations can be made in the disclosed systems and processes without departing from the scope of the disclosure. For example, the retrieval devices disclosed could include more or fewer arms. Other embodiments of the disclosure will be apparent to those skilled in the art from consideration of the specification and practice of the features disclosed herein. It is intended that the specification and examples be considered as exemplary only.

We claim:

1. A retrieval device, comprising:
   a sheath;
   an end-effector, the end-effector including:
      a plurality of arms including a first arm, a second arm, and a third arm; and
      a plurality of moveable members indirectly coupling the plurality of arms to the sheath, wherein a first moveable member of the plurality of moveable members extends between a distal end of the first arm to a distal end of the second arm, wherein a second moveable member extends between the distal end of the second arm to a distal end of the third arm, and wherein a third moveable member extends between the distal end of the third arm to the distal end of the first arm; wherein each arm of the plurality of arms includes a side wall opening; and
   a positioner located radially between the plurality of arms.

2. The retrieval device of claim 1, wherein each of the plurality of moveable members includes a plurality of pre-formed bends.

3. The retrieval device of claim 2, wherein the plurality of pre-formed bends includes three pre-formed bends.

4. The retrieval device of claim 1, wherein the end-effector includes a contracted configuration and an expanded configuration, wherein in the expanded configuration, each of the plurality of arms is radially expanded relative to a longitudinal axis of the sheath.

5. The retrieval device of claim 1, wherein the positioner includes a plurality of positioner members, wherein a first positioner member of the plurality of positioner members extends through the side wall opening of the first arm, a second positioner member of the plurality of positioner members extends through the side wall opening of the second arm, and a third positioner member of the plurality of positioner members extends through the side wall opening of the third arm.

6. The retrieval device of claim 5, wherein each of the plurality of positioner members is at least partially received within a lumen of the sheath.

7. The retrieval device of claim 1, wherein at least some of the plurality of arms includes a serrated edge.

8. A retrieval device, comprising:
a sheath;
an end-effector, the end-effector including:
- a plurality of arms, each of the plurality of arms including a proximalmost end positioned distally of a distalmost end of the sheath; and
- a plurality of moveable members extending between distal ends of the plurality of arms, wherein the end-effector includes a contracted configuration and an expanded configuration, wherein in the expanded configuration, each of the plurality of arms is radially expanded relative to a longitudinal axis of the sheath; wherein each arm of the plurality of arms includes a side wall opening positioned axially between the proximalmost and a distal end thereof; and
a positioner located radially between the plurality of arms.

9. The retrieval device of claim 8, wherein the positioner includes a plurality of positioner members, wherein a first positioner member of the plurality of positioner members extends through the side wall opening of a first arm of the plurality of arms, a second positioner member of the plurality of positioner members extends through the side wall opening of a second arm of the plurality of arms, and a third positioner member of the plurality of positioner members extends through the side wall opening of a third arm of the plurality of arms.

10. The retrieval device of claim 9, wherein each of the plurality of positioner members is at least partially received within a lumen of the sheath.

11. The retrieval device of claim 8, wherein each of plurality of moveable members includes a plurality of pre-formed bends.

12. A retrieval device, comprising:
a sheath; and
an end-effector, the end-effector including:
- a plurality of arms;
- a plurality of moveable members extending between distal ends of the plurality of arms; and
- a positioner located radially between the plurality of arms, wherein the positioner includes a plurality of positioner members extending through side openings of the plurality of arms and at least partially received within a lumen of the sheath.

13. The retrieval device of claim 12, wherein each of plurality of moveable members includes three pre-formed bends.

14. The retrieval device of claim 12, wherein at least some of the plurality of arms includes a serrated edge.

15. The retrieval device of claim 12, wherein the end-effector includes a contracted configuration and an expanded configuration, wherein in the expanded configuration, each of the plurality of arms is radially expanded relative to a longitudinal axis of the sheath.

16. The retrieval device of claim 12, wherein proximal ends of the plurality of arms are spaced from a distal end of the sheath.

* * * * *